United States Patent [19]

Muench et al.

[11] 4,205,188

[45] May 27, 1980

[54] PROCESS FOR THE PRODUCTION OF HYDROXYBENZYL ALCOHOLS

[75] Inventors: Wayne C. Muench; Thad S. Hormel; Pamela M. Kirchhoff; Lanny A. Robbins, all of Midland, Mich.

[73] Assignee: The Dow Chemical Company, Midland, Mich.

[21] Appl. No.: 940,698

[22] Filed: Sep. 8, 1978

[51] Int. Cl.$^2$ .............................................. C07C 37/24
[52] U.S. Cl. .................................. 568/764; 568/749; 568/432; 568/426
[58] Field of Search ................. 260/600; 568/764, 749

[56] References Cited

U.S. PATENT DOCUMENTS

| | | | |
|---|---|---|---|
| 2,839,587 | 6/1958 | Raum | 568/764 |
| 4,119,671 | 10/1978 | Bauer et al. | 260/600 R |

OTHER PUBLICATIONS

Hickinbottom, Reactions of Organic Compounds (1936), p. 102.
Eapen et al., Die Makromolekulare Chemie, vol. 119, No. 2766 (1968) pp. 4–16.

*Primary Examiner*—Bernard Helfin
*Attorney, Agent, or Firm*—Joyce P. Hill; Lester J. Dankert

[57] ABSTRACT

A process is provided for the production of hydroxybenzyl alcohols, comprising condensing phenol with formaldehyde in an alkaline solution to form a mixture of ortho- and para-hydroxymethyl phenols, and solvent extracting unreacted phenol from the resulting alkaline hydroxybenzyl alcohol condensate solution. The phenol-reduced hydroxybenzyl alcohol condensate solution is particularly suited for treatment with excess caustic and subsequent oxidation of the resulting aqueous solution of ortho- and para-hydroxybenzyl alcohols-sodium salt to yield the corresponding ortho- and para-hydroxybenzaldehydes-sodium salt.

3 Claims, No Drawings

PROCESS FOR THE PRODUCTION OF HYDROXYBENZYL ALCOHOLS

BACKGROUND OF THE INVENTION ortho-Hydroxybenzyl alcohol (saligenin) and para-hydroxybenzyl alcohol (homosaligenin) are produced from the alkali-catalyzed reaction of formaldehyde with phenol (Lederer, *J. Pr. Chem.*, 1894 [ii], 50, 223; Manasse, *Berichte*, 1894, 27, 2409; 1902, 35, 3844). The condensation reaction of phenol and formaldehyde can be run using a phenol/formaldehyde mole ratio of 1/1 or 2/1 (Hickinbottom, W. J., *Reactions of Organic Compounds*, Longmans, Green, London, England (1936) p. 102); the concentration of phenol is preferably kept higher than that of formaldehyde in order to avoid the formation of other than the desired products (Eapen, K. C. and L. M. Yeddanapalli, *Die Makromolekular Chemie*, Vol. 119 No. 2766 (1968) pp. 4–16). Whenever an excess of phenol is used, the unreacted phenol must be removed. The instant invention discloses a novel process for the production of hydroxybenzyl alcohols or hydroxybenzaldehydes comprising the removal of excess phenol from the resulting hydroxybenzyl alcohol condensate solution. It is particularly advantageous to use the aforementioned hydroxybenzyl alcohol condensate solution, without further purification, in the production of the corresponding aldehydes. Aldehydes which are the oxidation products of the alcohols having the reduced phenol levels can be purified simply, because the phenol levels are sufficiently low. Otherwise, costly and tedious steam distillations may be required primarily due to large amounts of excess phenol present in the crude condensate solution. Reduction of phenol also lowers the total organics and hence lowers the waste salt produced in the preparation of the aldehydes.

SUMMARY OF THE INVENTION

Excess phenol is removed from the crude reaction mixture resulting from the alkali-catalyzed condensation of phenol with formaldehyde using a solvent extraction process wherein phenol is selectively removed from the alkaline crude reaction mixture with an organic solvent, such as methyl isobutyl ketone. The reaction products, ortho- and para-hydroxybenzyl alcohols, are converted to salts by the addition of excess caustic, but remain in the aqueous phase from which they can be easily purified or oxidized to the corresponding aldehydes.

Detailed Description of the Invention

The alkali-catalyzed condensation of phenol with formaldehyde to produce ortho- and para-hydroxybenzyl alcohols (saligenin and homosaligenin, respectively) may be carried out in any conventional manner reported in the prior art. The reaction is known as the saligenin process or Lederer-Manasse reaction. Further, the saligenin process offers the possibility of phenol removal at a much earlier stage and hence simplifies the aldehyde product purification.

A variation in the quantity of phenol, formaldehyde, caustic, water, and a variation in the temperature of the reaction can be used advantageously to afford flexible ortho-/para-ratios of the alcohol product and optimum yields. The temperature of the reaction can be from 20° C. to 100° C., preferably 45° C. to 75° C. Lower temperatures reduce the reaction rate, higher temperatures can partially decompose the alcohol products. The reaction is generally run for from 0.5 to 3 hours. An analysis of the hydroxybenzyl alcohol condensate solution reveals varying concentrations of phenol, ortho-hydroxybenzyl alcohol, para-hydroxybenzyl alcohol, dihydroxymethyl phenols and highers.

It is desirable to remove the excess phenol from the aforementioned hydroxybenzyl alcohol condensate solution to facilitate the purification of the alcohol products or to prepare the alcohol for oxidation to the aldehyde. For this purpose, a solvent extraction method in an aqueous medium containing an alkaline reagent solution is employed. In this context, sodium hydroxide or potassium hydroxide (if cost is not a limiting factor) is generally employed as the alkaline reagent. The amount of alkaline reagent to be added is based on the total concentration of saligenins and by-product alcohols in the crude condensate solution. The extraction process is operable in a wide range of caustic/alcohol ratios from slightly less caustic than the total concentration of saligenins and by-product alcohols to considerably more; caustic/alcohol molar ratios of approximately 1/1 are preferred for the removal of phenol in a continuous or batch-wise manner. The addition of caustic is preferably done at room temperature.

Solvents, very selective for phenol, are known. A preferred organic solvent is immiscible and inert in the aqueous phase, or is more volatile than water, or forms an azeotrope with water. Exemplary classes of compounds which are suitable solvents for the liquid phase extraction are, ethers, esters, ketones, aromatic hydrocarbons, alcohols, chlorinated hydrocarbons and the like. Specific examples of such solvents are chloroform, toluene, cyclohexanol, n-hexanol, chlorobenzene, methyl isobutyl ketone and methyl ethyl ketone. The solvents of choice, methyl isobutyl ketone (MIBK), and methyl ethyl ketone (MEK) are found to work well with saligenin crude if the caustic concentration is properly adjusted. Solvents are generally used alone although suitable combinations of two or more solvents can be used. This invention is not limited to the use of a particular solvent; incorporated herein by reference are the organic solvents which have a preferential selectivity for phenol as described in C. Golumbie et al., U.S. Pat. No. 2,581,406; H. L. Grimmett et al., U.S. Pat. No. 2,807,654; H. Merkel, U.S. Pat. No. 3,155,734; Anwar et al., "Improved Dissociation Extraction Process for the Separation of Acidic or Basic Organic Isomers", *Proc. Inst. Sol. Ext. Conf.*, II 911–919 (1971).

Representative data for MIBK extraction of saligenin crude as a function of caustic concentration are presented in Table I. The partition coefficient (m) values decrease and the selectivities ($\beta$) increase with increasing caustic concentration. As a result, there is greater selectivity of phenol to the organic MIBK layer and greater selectivity of the alcohol products to the aqueous raffinate. This indicates that by a judicious choice of caustic/feed ratio and by running countercurrent, most if not all phenol can be removed. For typical batch operations, with high selectivities, phenol levels are reduced to 3 to 5 percent using saligenin crude with 24 weight percent phenol. Successive and repetitive extractions of the aqueous saligenin crude removes some of the saligenins along with the unreacted phenol. The extracted saligenins can be recovered from the organic solution by back-extraction with caustic. Scale-up operations using a countercurrent extractor reduced the level of phenol in the saligenin condensate to below 1 weight percent.

TABLE I

Effect of NaOH Concentration on MIBK Extraction of Saligenin Crude[1]

| | Sample No. 1 | | | Sample No. 2 | | | Sample No. 3 | | |
|---|---|---|---|---|---|---|---|---|---|
| | Initial Assay | Extraction Assay | | Initial Assay | Extraction Assay | | Initial Assay | Extraction Assay | |
| | | MIBK | Aqueous | | MIBK | Aqueous | | MIBK | Aqueous |
| Phenol ($\phi$OH) | 24.04 | 14.7 | 3.4 | 21.11 | 14.08 | 4.74 | 15.8 | 12.4 | 4.6 |
| o-Hydroxybenzyl alcohol (o-Salg) | 8.65 | 3.3 | 6.42 | 7.42 | 2.24 | 6.91 | 6.4 | 1.4 | 5.6 |
| p-Hydroxybenzyl alcohol (p-Salg) | 4.77 | 1.10 | 5.79 | 4.50 | 0.65 | 5.62 | 4.7 | 0.4 | 5.0 |
| By-product alcohols | 6.74 | 0.3 | 10.46 | 6.0 | 0.15 | 7.65 | 3.5 | 0.1 | 4.8 |
| Molar ratio of NaOH to Phenolic Compounds in Saligenin Crude | | 0.27 | | | 0.37 | | | 0.44 | |
| Partition Coefficient (m)[2] | | 4.3 | | | 3.0 | | | 2.7 | |
| Selectivity for ortho- ($\beta$o)[3] | | 8.3 | | | 9.2 | | | 10.8 | |
| Selectivity for para- ($\beta$p)[4] | | 22.8 | | | 25.7 | | | 33.7 | |

Footnotes:
[1] Saligenin crude containing concentrations of phenol, ortho-hydroxybenzyl alcohol, para-hydroxy-benzyl alcohol and by-product alcohols (i.e., 2,4-dihydroxymethyl phenol), in percent by weight.

[2] $m$ (Wt. %) $= \dfrac{(\phi OH) \text{ MIBK}}{(\phi OH) \text{ Aqueous}}$

[3] $\beta o$ (Wt. %) $= \dfrac{(\phi OH/o\text{-Salg}) \text{ MIBK}}{(\phi OH/o\text{-Salg}) \text{ Aqueous}}$

[4] $\beta p$ (Wt. %) $= \dfrac{(\phi OH/p\text{-Salg}) \text{ MIBK}}{(\phi OH/p\text{-Salg}) \text{ Aqueous}}$ At temperatures above 25° C., MIBK extractions give faster phase separations, about 30 seconds to about 10 seconds, and clearer phases; a slight haze is noticed in both phases at 25° C. From a total energy standpoint, it is preferred to run the MIBK extraction in the same preferred temperature range of the phenol-formaldehyde condensation reaction, 45° C. to 75° C. Extraction with MEK is performed at elevated running temperatures of 50° C. to 60° C. The increase in temperature provides better phase separation.

In general, an organic solvent of choice can be used to make successive and repetitive extractions of the crude, aqueous phenol-formaldehyde condensation solution in a batch-wise or continuous manner until the unreacted phenol is reduced to the desired level. Each successive aqueous extract phase contains less phenol than the previous one until a relatively phenol-free aqueous solution and a phenol-enriched organic solvent result. In a batch process, some of the saligenins are extracted along with the unreacted phenol. Back-extraction with caustic is used to recover the saligenins in the organic solvent extract. The recovered saligenins can be combined with the phenol-reduced aqueous extract for subsequent oxidation to the corresponding hydroxybenzaldehydes.

In a continuous process having a countercurrent flow in a single column, the organic solvent stream is fed to the bottom of the column while aqueous caustic and saligenin condensate are fed into the top of the column. Under agitated conditions, during which the condensate and caustic flow downward, the organic solvent works its way upward through the column and selectively removes unreacted phenol from the saligenin condensate. The saligenins and by-product alcohols remain in the aqueous phase created by the aqueous caustic solution that flows downward and exits from the bottom of the column. The phenol-enriched organic solvent exits from the top of the column and is initially treated with caustic to recover saligenins that have been extracted with phenol. A second treatment of the organic solvent with caustic follows to remove more of the organic materials. Phenolics are then separated from the organic solvent via distillation; both the purified MIBK and phenolics are reuseable. The phenol-reduced aqueous saligenin crude is now available for other uses and is particularly suited for oxidation to the corresponding hydroxybenzaldehydes.

The following examples are given to illustrate the method of this invention; however, the specific details of these examples are not to be taken as limitations upon the invention. In the examples which follow, and throughout the specification, the quantities of material are expressed in terms of parts and percent by weight, unless otherwise specified.

EXAMPLE 1

Phenol Extraction with MIBK

To a five-liter round bottom flask were added 77.32 parts of 97 percent NaOH, 868.2 parts water, and 802.7 parts of 88 percent phenol (containing 96.2 parts water). This resulted in a clear solution which was heated to 45° C. before the rapid addition of 237.7 parts of 37.9 percent formaldehyde (containing 115.52 parts water). The temperature was maintained at 45° C.-50° C. for one hour and then cooled to room temperature (about 23° C.). Analysis of this crude reaction mixture by vapor phase chromatography (VPC) with internal standard gave the condensation crude assay reported in Table II below. The overall yield of o- and p-hydroxybenzyl alcohol based on the phenol consumed is 75 percent.

The crude reaction mixture above is then treated with 20.4 parts of 97 percent NaOH dissolved in 35 parts water and then is extracted three times with 777 parts, 469 parts, and 304 parts, respectively, of methyl isobutyl ketone (MIBK). 2165 Parts of MIBK extract and 1387 parts of extracted aqueous solution are obtained. The VPC analyses of the resulting organic (MIBK) and aqueous layers are compared with the VPC analysis of the condensation crude in Table II below. The saligenins dissolved in the MIBK are removed by back-extraction with caustic solution. The resulting phenol-containing MIBK is also back-extracted with a subsequent batch of aqueous caustic to remove as much phenol as possible and then is distilled to separate phenolics from MIBK for subsequent reuse. The extracted aqueous layer containing the o- and p-hydroxybenzyl alcohols is suitable for oxidation to the corresponding hydroxybenzaldehydes.

TABLE II

| Component | Assay in Weight Percent | | |
|---|---|---|---|
| | Condensation Crude | MIBK Extract Layer | Agueous Layer |
| Phenol | 24.2 | 16.9 | 3.1 |
| o-hydroxy-benzyl alcohol | 7.1 | 2.62 | 5.4 |
| p-hydroxy-benzyl alcohol | 4.2 | 0.7 | 4.6 |
| dihydroxy-methyl phenol & highers | 4.8 | 0.2 | 4.0 |

The above data reveal the efficient manner in which the MIBK extraction process selectively removes unreacted phenol from the aqueous saligenin crude while leaving the saligenins and by-product alcohols in the aqueous layer.

EXAMPLES 2-3

Phenol Extraction with MEK

In a one-liter round bottom flask are added 10 parts of 50 percent NaOH, 85.8 parts water, and 94.09 parts 88 percent phenol. This mixture is heated with stirring to 70° C. prior to the addition of 11.5 parts of 38 percent formaldehyde. The temperature is maintained at 70° C. for one hour with continuous stirring and then cooled to room temperature (about 23° C.). Analysis of the above condensation reaction mixture by VPC with internal standard appears in column (1) of Table III below. The crude reaction mixture is then extracted twice with 203 parts and 68 parts respectively of methyl ethyl ketone (MEK) at 25° C. 369.01 Parts of MEK extract is obtained and analyzed as shown in column (2) of Table III below. A portion of the combined MEK extract is back-extracted with caustic to recover some of the saligenins that are removed along with phenol. To accomplish the back-extraction, 0.085 mole of NaOH is added to 50.2 parts water to form a caustic solution which is subsequently added to a portion of the combined MEK extract layers. The moles of NaOH added is equal to the total moles of mono- and di-alcohol products calculated to be in the combined layers of MEK used in the back-extraction. 57 Parts caustic solution (6.8 parts 50 percent NaOH and 50.2 parts water) are added to 364 parts of the combined MEK extract layers and are stirred for 15 minutes, then allowed to separate. A VPC analysis of the separate layers is recorded in columns (3) and (4) of Table III.

In substantially the same manner as described above, 20 parts of 50 percent NaOH, 70.59 parts water and 106.94 parts of 88 percent phenol are heated with stirring prior to the addition of 31.58 parts of 38 percent formaldehyde. Analysis of the above reaction mixture by VPC with internal standard is reported in Table III Column (1) of Example 3. After two extractions with 240 parts MEK and 80 parts MEK respectively, the MEK layers are combined and analyzed for phenol and saligenin content as shown in Table III, Column (2) of Example 3. A back-extraction of the combined MEK layers is done with 10 parts caustic, 72 parts water and 479 parts of the combined MEK extract layers. The caustic solution and MEK extract layers are stirred together for 15 minutes and then allowed to separate into an aqueous layer and a MEK extract layer. A VPC analysis of the two layers from the back-extraction step is reported in Table III, Columns (3) and (4) of Example 3.

The reported VPC analyses demonstrate the ability of MEK to remove phenol from the condensation crude in a process involving two extractions with MEK and one back-extraction with caustic.

TABLE III

| | | MEK Extraction - Assay in Weight Percent | | | |
|---|---|---|---|---|---|
| | | | | Back-Extraction | |
| Example No. | Component | Condensation Crude (1) | Combined MEK Extract Layer (2) | MEK Layer (3) | Aqueous Layer (4) |
| 2 | phenol | 39.26 | 18.41 | 17.64 | 9.05 |
| | o-hydroxybenzyl alcohol | 5.39 | 1.93 | 1.50 | 3.08 |
| | p-hydroxybenzyl alcohol | 2.65 | 0.81 | 0.51 | 1.68 |
| | dihydroxy-methyl phenol | 1.27 | 0.19 | 0.06 | 0.67 |
| 3 | phenol | 29.57 | 13.69 | 12.28 | 11.65 |
| | o-hydroxybenzyl alcohol | 9.28 | 3.67 | 2.28 | 4.53 |
| | p-hydroxybenzyl alcohol | 3.41 | 1.75 | 0.85 | 2.22 |
| | dihydroxy-methyl phenol | 3.57 | 1.41 | 0.53 | 2.11 |

The aqueous layer containing o- and p-hydroxybenzyl alcohols is suitable for oxidation to the corresponding hydroxybenzaldehydes using oxidation processes known in the art which are suitable for the conversion of primary alcohols to aldehydes.

EXAMPLE 4

Pilot plant extractions are performed at room temperature (about 23° C.) in a countercurrent extractor equipped with an internal agitator. The aqueous saligenin condensate stream is fed into the column at a point three-fourths of the distance from the bottom to the top, the solvent is added at the bottom and the caustic is introduced near the top of the column. Streams entering the column are metered with piston pumps.

An experiment using MIBK as the solvent, is conducted as follows: the countercurrent extractor is filled initially with MIBK and 5 percent NaOH. An aqueous saligenin condensate stream is then fed into the column at a point three-fourths of the way from the bottom to the top of the column and the desired running conditions are obtained. The aqueous phase is the continuous phase. A steady state run is made under the following conditions. The saligenin condensate containing by weight 23.9 percent phenol, 7.4 percent o-hydroxybenzyl alcohol, 4.2 percent p-hydroxybenzyl alcohol, 4.6 percent 2,4-dihydroxymethyl phenol is fed at 14.5 lbs/hour. MIBK is fed at 10.0 lbs/hour, and 5 percent NaOH is fed at 5.1 lbs/hour. The agitation intensity in this example, (rpm multiplied by stroke length), divided by plate spacing, is 14, but can be varied by one skilled in the art so that there is mild agitation within the column. Under steady state conditions a weight percent analysis of MIBK extract and aqueous raffinate samples revealed:

|  | Phenol | o-hydroxy-benzyl alcohol | p-hydroxy-benzyl alcohol | DiOH |
|---|---|---|---|---|
| aqueous Raffinate | 1.4 | 5.0 | 3.7 | 3.7 |
| MIBK Extract | 22.6 | 1.9 | 0.1 | 0.01 |

From the above examples it is evident that it is possible to separate phenol from hydroxy-substituted benzyl alcohol mixtures by countercurrent or batch-wise extraction in which there is a multiplicity of transfers and wherein the system is an organic solvent possessing solvent properties for the unsubstituted phenol and an aqueous alkaline medium possessing different solvent properties for the hydroxy-substituted benzyl alcohols such as, o-hydroxybenzyl alcohol, p-hydroxybenzyl alcohol, and 2,4-dihydroxymethyl phenol.

What is claimed is:

1. In a process for the production of mixtures of ortho- and para-hydroxybenzyl alcohols formed during the sodium hydroxide-catalyzed condensation of phenol with aqueous formaldehyde in an alkaline solution, the improvement comprising the solvent extraction of unreacted phenol from the alkaline solution containing the hydroxybenzyl alcohol condensate, at temperatures between about 20° C. and about 60° C., with solvents selected from the group consisting of methyl ethyl ketone, methyl isobutyl ketone, and mixtures thereof.

2. The process improvement of claim 1 wherein the solvent used in the solvent extraction is methyl isobutyl ketone.

3. The process improvement of claim 2 wherein the solvent extraction is conducted when the molar ratio of sodium hydroxide to phenol in the hydroxybenzyl alcohol condensate is from about 0.25 to about 0.45.

* * * * *